US00PP36419P2

(12) United States Plant Patent
Hatterman-Valenti et al.

(10) Patent No.: US PP36,419 P2
(45) Date of Patent: Feb. 4, 2025

(54) GRAPE PLANT NAMED 'ND213'

(50) Latin Name: ***Vitis* spp. hybrid**
Varietal Denomination: ND213

(71) Applicant: NDSU RESEARCH FOUNDATION, Fargo, ND (US)

(72) Inventors: Harlene M. Hatterman-Valenti, Fargo, ND (US); John E. Stenger, Fargo, ND (US)

(73) Assignee: NDSU RESEARCH FOUNDATION, Fargo, ND (US)

( * ) Notice: Subject to any disclaimer, the term of this patent is extended or adjusted under 35 U.S.C. 154(b) by 0 days.

(21) Appl. No.: 18/417,824

(22) Filed: Jan. 19, 2024

(51) Int. Cl.
*A01H 5/08* (2018.01)
*A01H 6/88* (2018.01)

(52) U.S. Cl.
USPC ..... Plt./207

(58) Field of Classification Search
USPC ..... Plt./205, 206, 207
See application file for complete search history.

(56) References Cited

U.S. PATENT DOCUMENTS

PP16,478 P3 4/2006 Luby et al.

*Primary Examiner* — Susan McCormick Ewoldt
(74) *Attorney, Agent, or Firm* — McKee, Voorhees & Sease, PLC

(57) ABSTRACT

The grape plant cultivar 'ND213' is a red wine grape for white wine production which exhibits superior cold hardiness and disease resistance.

3 Drawing Sheets

STATEMENT REGARDING FEDERALLY SPONSORED RESEARCH

This invention was made with government support under NI18HMFPXXXXG008, NI19HMFPXXXXG008, NI22HMFPXXXXG015, NI21HMFPXXXXG018, and NI20HMFPXXXXG005 awarded by the United States Department of Agriculture's National Institute for Food and Agriculture (USDA-NIFA) and AM200100XXXXG063 awarded by the United States Department of Agriculture's Agricultural Marketing Service (USDA-AMS). The government has certain rights in the invention.

Botanical designation:

Genus and species: *Vitis* spp. hybrid.

Variety denomination: The new plant has the varietal denomination 'ND213'.

BACKGROUND

Most grape varieties used for production of high quality wines around the world are of the species *Vitis vinifera*. These *V. vinifera* varieties, when cultivated in northern regions of the United States with a continental climate, are often subject to serious injury or death from low temperatures during winter. Although several wild *Vitis* species occur in colder regions of North America and eastern Asia, the wine made from these species generally has serious defects. Thus, there is a need for grape varieties that are winter hardy yet produce fruit capable of yielding high quality wine.

BRIEF SUMMARY

'ND213' is a variety of red grape (*Vitis* hybrid) suitable for white wine production and is well adapted to the Upper Midwest climate of the United States. 'ND213' exhibits a high level of cold hardiness, with trunks having survived −38° C. 'ND213' showed limited cold temperature dieback (winter injury) in comparison to the cold hardy gris wine grape 'Frontenac Gris' (U.S. Plant Pat. No. 16,478). The fruit of 'ND213' produces a good quality, well balanced wine with good body, attractive color, and notes of apple, citrus, stone fruit, grapefruit, and tropical fruit. 'ND213' exhibits good disease resistance, showing low susceptibility to powdery mildew (*Uncinula necator*), downy mildew (*Plasmopara viticola*), black rot (*Guignardia bidwellii*), and foliar phylloxera (*Daktulosphaira vitifoliae*).

'ND213' originated from a hand-pollinated cross of 'C-16' (female parent, not patented) and 'Alpenglow' (male parent, not patented) made in 2008. Asexual propagation of the new cultivar was accomplished by rooting dormant hardwood cuttings in 2015 in Fargo, ND. Asexual propagation of the cultivar by dormant hardwood cuttings has determined that the characteristics are stable and true to type in successive generations. 'C-16' arose from a cross between *Vitis* 'Severnji' and a *Vitis riparia* male pollen parent.

DETAILED BOTANICAL DESCRIPTION

Figure 1:
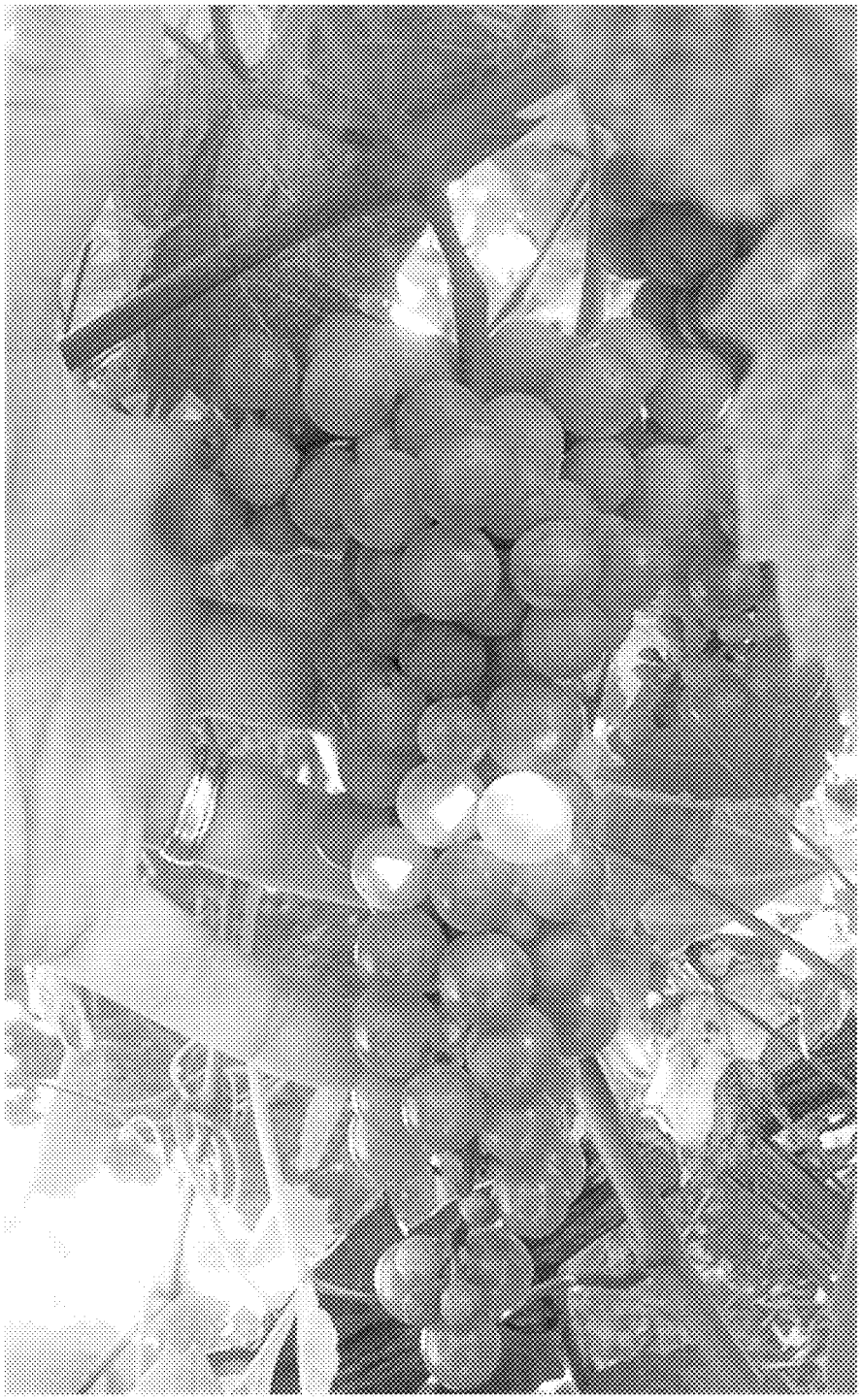
FIG. 1 is a photograph taken in 2014 of a 'ND213' fruit cluster on three-year-old vines grown in Fargo, ND.
Figure 2:
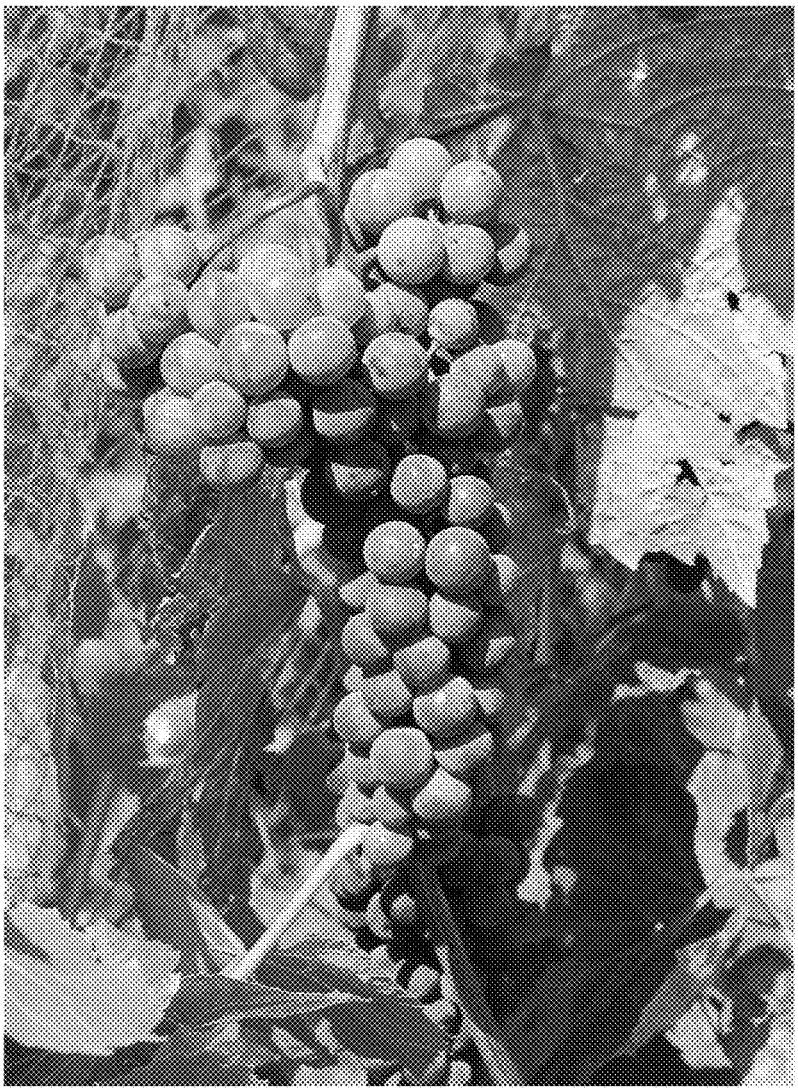
FIG. 2 is a photograph taken in 2018 of a 'ND213' fruit cluster on two-year-old vines grown near Absaraka, ND.
Figure 3:
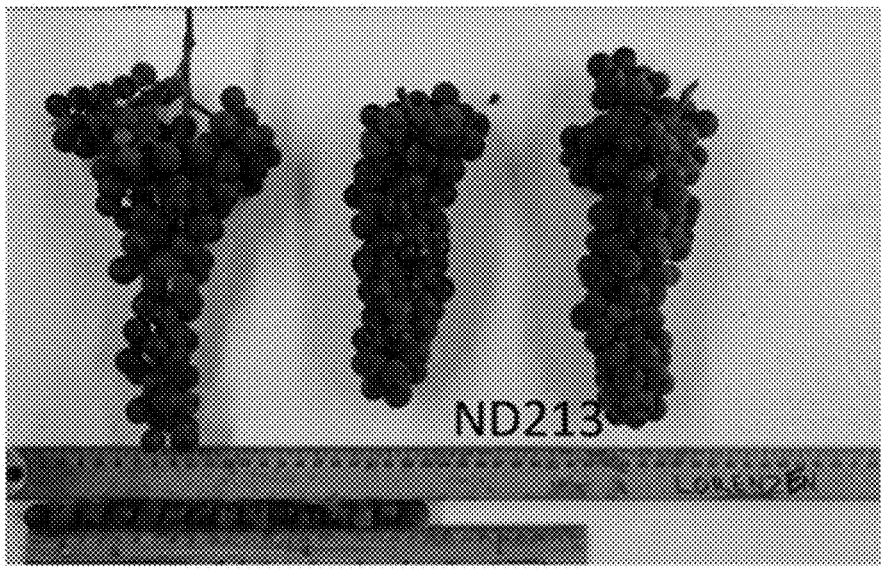
FIG. 3 is a photograph taken in 2014 of harvested 'ND213' fruit from three-year-old vines grown in Fargo, ND.

'ND213' differs from male parent, 'Alpenglow', in that 'ND213' has a longer looser cluster with a more pronounced first lateral branch. 'ND213' stems were also more vigorous, and berries ripened to a deeper red. Data collected in 2018 in Fargo, ND reinforced observations where both cultivars were growing, but not in the same trial, with 'ND213' having 112% greater cluster weight and 2% greater berry weight than 'Alpenglow'. Female parent, 'C-16', has not been characterized and plant material is unavailable for characterization. Thus, comparison to the female parent is not possible.

The following is a detailed botanical description of the new variety of grape plant, its flowers, fruit, foliage etc. as based on observations of various aged specimens grown in Absaraka, ND and Fargo, ND over the 2016-2021 growing seasons. All color references are taken from The Royal Horticultural Society (R.H.S.) Colour Chart, 5th Edition.

TABLE 1

| Trait | Value |
|---|---|
| Botanical classification: | Cultivar of *Vitis* with ancestry from several species including, *V. vinifera*, *V. riparia*, *V. labrusca*, and *V. amurensis*. |
| Parentage: | 'C16' (female), 'Alpenglow'(male). |
| General Characteristics | |
| Mature canes: | The observations are the means of 10 canes observed from the 2019 to 2021 growing seasons. |
| Color of canes. | Dark 175B strips, contrasting with between 165B and 164C light strips |
| Length of canes. | 1.24 m (0.66-2.24) |
| Diameter of canes. | 8.1 mm (stdev 1.7 mm) |
| Internode length | 51.3 mm (stdev 31.2 mm) |
| Lenticels | Yes, small <1 mm length. |
| Cane cross-section shape. | Circular to ovate. |
| Density of hairs on mature cane. | Absent. |
| Tendril pattern on shoot | 2,0,2,0; two nodes with tendrils followed by one node without. |
| Tendrils forked | Yes |
| Tendril texture | Striated |
| Tendril color | N144C |
| Bud width | 3.6 mm (2.5-4.5 mm) |
| Bud length | 5.3 mm (4.2-7.0 mm) |
| Bud shape | Triangular. |
| Bud color | Between 165 A and 166 B. |
| Trunk: | The observations of trunk characteristics presented are from the 2019 growing season. |
| Bark texture | Somewhat flaky, small vertical segments below 5 mm in width and length. |
| Bark color. | Between 161B and 165B |
| Mature leaves | Ten representative mature leaves were collected from above the cluster at each growing location. The leaves were pressed and dried for analysis. The values presented are means from leaves collected in Absaraka, ND and Fargo, ND in 2020. Descriptors of mature leaves relate to OIV descriptor list for grape varieties and Vitis species (OIV, International Organisation of Vine and Wine, Technical document ). |
| Length of blade. | 12.9 cm (10.6-16.4) |
| Width of blade. | 14.8 cm (10.4-18.3) |
| Shape of blade. | Cuneiform, wedge-shaped |
| Number of lobes. | Three to five. |
| Blade margins. | Incised into three to five lobes. |
| Length of primary (midrib) vein N1 from the tip of the blade to the petiole sinus. | 127 mm (stdev 21 mm) |
| Length of vein N2 from the tip of the first major lobe of the blade to the petiole sinus. | 111 mm (stdev 18 mm) |

TABLE 1-continued

| Trait | Value |
|---|---|
| Length of vein N3 from the tip of the second major lobe of the blade to the petiole sinus. | 77 mm (stdev 14 mm) |
| Length of vein N4 from the tip of the third major lob of the blade to where it joins the vein measured in N3. | 42 mm (stdev 8 mm) |
| Length of vein N5 from the tip of the first tooth proximal to the petiole sinus to where it joins the vein measured in N4. | 17.6 mm (stdev 4.1 mm) |
| Length of N2 teeth. | 11.2 mm (stdev 3.8 mm) |
| Width of N2 teeth. | 14.6 mm (stdev 3.9 mm) |
| Length/width ratio of N2 teeth. | 0.77 |
| Length of N4 teeth. | 5.6 mm (stdev 2.1 mm) |
| Width of N4 teeth. | 11.3 mm (stdev 1.6 mm) |
| Length/width ratio of N4 teeth. | 0.5 |
| Shape of teeth. | both sides straight |
| Shape of petiolar sinus. | Open to very-open |
| Shape of base of petiolar sinus. | U-shaped |
| Depth of petiolar sinus. | 43.1 mm (stdev 9.0 mm) |
| Width of petiolar sinus. | 61.0 mm (stdev 16.9 mm) |
| Petiole. | 2.5 mm diameter. Length 101.7 mm (24.6 mm stdev) |
| Shape of upper sinuses. | General absence of upper sinus, urn-shaped when present. |
| Shape of base of upper sinuses. | V-shaped |
| Pubescence on adaxial surface. | Slight. |
| Pubescence on abaxial surface. | Small erect hairs. |
| Color of adaxial leaf surface. | 146B |
| Color of abaxial leaf surface. | 143B, vein 154A and 1.5-0.9 mm thick, anthocyanins absent except near base of main vines - 46C |
| Color of leaf petiole. | 58A, 184C |
| Center lobe size. | Length 4.5 cm; width 7.6 cm. |
| Lateral lobe size. | Length 2.1 cm; width 3.3 cm. |
| Basal lobe size. | Length 1.1 cm; width 1.9 cm. |
| Young shoots: | |
| Form of shoot tip. | Open. |
| Density of prostrate hairs on tip. | Moderate pubsecence. |
| Density of erect hairs on tip. | Sparse |
| Petiole pigmentation | 144A-144C |
| Shoot attitude. | Semi-procumbent |
| Shoot pigmentation (internodes and nodes). | 143A-143B |
| Young leaves. | abaxial: 144C, adaxial: 144B |
| Flowers: | |
| Fragrances. | Moderately fragrant. |
| Mean time of flowering. | June 2 (May 29-June 10) when grown in Fargo, ND. |
| Color of calyx. | N144C. |
| Sepal number. | 5 sepals fused into a continuous calyx. |
| Calyx shape. | Ring shaped. |
| Calyx size. | 2.44 mm in length (1.9-3.1); 1.35 mm in diameter (1.1-1.6). |

TABLE 1-continued

| Trait | Value |
|---|---|
| Calyx apex. | Fused to ovary. |
| Calyx base. | Fused to pedicel. |
| Nectary. | 1.2 mm in diameter; <1 mm in length; color 153C. |
| Calyx surface. | Glabrous. |
| Petals. | 5 petals fused in calyptra. |
| Color of Petal. | Between 154A and N144C. |
| Shape of cluster. | Cyclindrical to conical, typically with one shoulder. |
| Size of cluster. | Length 90.9 mm (stdev 20.9); width 7.4 mm (stdev 2.4). |
| Number of flowers. | Average of 183 with up to 89 on wings if present. |
| Flower buds. | Length 3.9 mm; 2.5 mm width; color 143A to 146B. |
| Size of individual entire flower. | Flower length: 3.9 mm (stdev 0.5mm); flower width 1.1 mm (stdev 0.28). |
| Pollen fertility. | Fertile based on selfing and use as parent in controlled crosses. |
| Reproductive organs. | Fully developed stamens and gynoecium. |
| Color of stamen. | Anther: 20 C; filament: 163D. |
| Stamen number. | Average of 5. |
| Filament length. | 3.0 mm in length. |
| Anther. | <1 mm in length. |
| Pollen quantity and color. | Abundant, color between 13B and 15B. |
| Pistil. | 1 pistil present, ovary length 1.75 mm and 0.85 mm at base, urn-shaped. |
| Pedicel | 2.3 mm and <1 mm in width, color 150A. |
| Peduncle. | Peduncle length to base of cluster 12.2 cm (stdev 4.9 cm); peduncle width 3.0 cm (stdev 0.8 cm). |
| Peduncle Color. | Sun exposed peduncle between 61A and 58A, shaded peduncle between 150A and N144C. |
| Fruit. | |
| Cluster length. | 19.5 cm (11.5-28.2 cm) |
| Cluster diameter. | 9.2 cm (6.1-12.2 cm) |
| Cluster weight. | 175 g (120-309 g) |
| Cluster density. | Medium, based on Trait 204 of the International Organisation of Vine and Wine (OIV) Descriptor List for grape varieties and *Vitis* species, 2$^{nd}$ edition. |
| Berry weight. | 2.11 g (1.56-2.31 g) |
| Berry length. | 1.55 (1.32-1.65 cm) |
| Berry diameter at equator. | 1.49 (1.30-1.62 cm) |
| Berry shape. | Roundish. |
| Berry cross-section. | Circular. |
| Berry, color of skin. | Varying based on sun exposure with lighter, unexposed berries between 2B and 9A and darker, exposed berries between 65A and 77B. |
| Berry, color of flesh. | 8D. |
| Berry firmness. | Very firm. |
| Berry, particular flavor. | Neutral, subdued *V. larbusca* characteristic flavors. |
| Length of pedicel. | 4.5 mm (3.4 to 6.6 mm) |
| Pedicel diameter. | 1.5 mm (0.9 to 1.9 mm) |

TABLE 1-continued

| Trait | Value |
|---|---|
| Pedicel color. | 144C. |
| Berry, separation from pedicel. | Difficult. |
| Berry, presence of seeds. | Fully developed. |
| Seed number/berry. | 2.8 (1-4) |
| Seed length. | average 6.45 mm SD 0.64 |
| Seed width. | average 4.44 mm SD 0.298 |
| Seed length/width ratio. | 1.46 |
| Seed weight. | 0.05 grams |
| Seed color. | 164A |
| Fruit: | Values represent the means (with ranges in parentheses) for fruit harvested over five growing seasons, 2016-2020. |
| Harvest date. | 08/24 (08/12-09/16). |
| Brix. | 20.3 (18.4-21.2). |
| pH. | 3.40 (3.05-3.57) |
| Titratable acidity. | 8.8 (8.1-10.8) g/liter. |
| Vineyard performance: | Descriptions are based on field observations made over four years (2017-2020). |
| Susceptibility to powdery mildew (*Uncinula necator*). | Low |
| Susceptibility to downy mildew (*Plasmopara viticola*). | Low |
| Susceptibility to black rot (*Guignardia bidwellii*). | Low |
| Susceptibility to grey mold (*Botrytis cinerea*). | Not observed during evaluation. |
| Susceptibility to foliar phylloxera (*Daktulosphaira vitifoliae*). | Low |
| Susceptibility to crown gall (*Agrobacterium tumefaciens*). | Mildly susceptible, Infection observed for the first time in 2019 following severe winter temperatures. |
| Susceptibility to phenoxy herbicide drift. | Mildly susceptible |
| Berry splitting. | Very low |
| Berry shelling. | Very low |
| Vigor level. | Moderate to high. |
| Winter hardiness. | Moderate to high; trunks have survived -38° C. |
| Wood ripening. | Good. |
| Productivity. | Average yield between 8-24 lbs (3.6-10.9 kg) per plant based on pruning, spacing, and location. |

I claim:

1. A new and distinct grape plant cultivar designated ND213 substantially as described and illustrated herein.

* * * * *